United States Patent [19]

Weinstein

[11] 4,157,490

[45] Jun. 5, 1979

[54] X- AND Y-AXIS DRIVER FOR ROTATING MICROSPHERES

[75] Inventor: Berthold W. Weinstein, Livermore, Calif.

[73] Assignee: The United States of America as represented by the United States Department of Energy, Washington, D.C.

[21] Appl. No.: 906,818

[22] Filed: May 17, 1978

[51] Int. Cl.[2] ............................................. G05B 19/40
[52] U.S. Cl. ........................................ 318/685; 73/104
[58] Field of Search .................. 318/685, 560; 73/104, 73/105

[56] References Cited

U.S. PATENT DOCUMENTS 3,523,448  8/1970  Rozelaar et al. ...................... 73/104

Primary Examiner—B. Dobeck
Attorney, Agent, or Firm—Dean E. Carlson; R. S. Gaither; L. E. Carnahan

[57] ABSTRACT

Apparatus for precise control of the motion and position of microspheres for examination of their interior and/or exterior. The apparatus includes an x- and y-axis driver mechanism controlled, for example, by a minicomputer for selectively rotating microspheres retained between a pair of manipulator arms having flat, smooth end surfaces. The driver mechanism includes an apertured plate and ball arrangement which provided for coupled equal and opposite movement of the manipulator arms in two perpendicular directions.

5 Claims, 5 Drawing Figures

X- AND Y-AXIS DRIVER FOR ROTATING MICROSPHERES

BACKGROUND OF THE INVENTION

The invention described herein was made at the Lawrence Livermore Laboratory in the course of, or under, Contract No. W-7405-ENG-48 between the United States Department of Energy and the University of California.

The invention relates to fabrication of inertial confinement fusion targets, particularly to the examination of spherical members utilized in such targets, and more particularly, to a driver mechanism for controllably rotating such spherical members.

The target most commonly employed in inertial confinement fusion development efforts is a hollow glass microsphere about 100 $\mu$m in diameter filled with a deuterium-tritium mixture. Theoretical calculations show that to achieve high density implosions, the targets require a high degree of symmetry, concentricity, and uniformity in surface finish.

One of the most difficult problems in the use of hollow glass microspheres for inertial confinement fusion targets is that of inspecting the entire wall of the tiny spheres for defects (uniformity of wall thickness and surface area). For the characterization of the surface and thickness of these tiny spheres (50 to 500 $\mu$m diameter) one requires a method of inspecting the entire surface area thereof with fast, repeatable positioning.

Prior apparatus for manipulating the microspheres has involved the use of vacuum chucks for holding same. The vacuum chuck apparatus involves a complex two-axis angular manipulator to position the microsphere for overall examination and it is difficult to align the two axes of rotation with each other and with the center of the sphere. With the vacuum chuck manipulator apparatus, in order to inspect the entire surface, the microsphere must be transferred from one chuck to another at least once, and such operation, in addition to the time involved, can mar the surface of the microsphere.

Recently, a manipulator for fast, repeatable positioning of the microsphere has been developed which utilizes a pair of smooth, flat, and preferable pliable surfaces at the ends of manipulator arms which retains the microsphere therebetween and which can roll the microsphere in two perpendicular horizontal directions without movement of the microsphere center. Such a manipulator arm arrangement is described and claimed in copending U.S. patent application Ser. No. 906,815, filed May 17, 1978, in the name of B. W. Weinstein et al, and assigned to the assignee of this application, and is incorporated herein by reference.

SUMMARY OF THE INVENTION

The present invention is directed to an x- and y-axis driver mechanism for manipulator arms which retain and rotate a spherical member for examination purposes, whereby precise control of the motion and position of the spherical member is provided. The driver mechanism includes a pair of movable driver plates and a fixed, apertured control plate having a plurality of spheres therein. Upon selected activation of a drive plate by an x-y table drive assembly, motion is produced in each of the two perpendicular (x-, y-) horizontal directions which in turn rotates the spherical member via manipulator arms secured to the movable driver plate. The driver mechanism thus provides a means for quickly and controllably rotating spherical members, such as microspheres utilized in inertial fusion targets, for examination of the surface and/or interior thereof.

Therefore, it is an object of this invention to provide an x- and y-axis driver for manipulating spherical members.

A further object of the invention is to provide an apparatus which provides precise control of the motion and position of a microsphere for examination thereof.

Another object of the invention is to provide a driver mechanism for spherical member manipulator arms so as to control rotation of the spherical member in each of two perpendicular horizontal directions.

Other objects of the invention, not specifically set forth above, will become readily apparent from the following description and accompanying drawings.

DETAILED DESCRIPTION OF THE PREFERRED EMBODIMENT

The invention involves a driver mechanism for control of the motion and position of a microsphere manipulator for examination of the microsphere by x-ray absorption, light transmission interference, or light reflection interferometry, etc.

The manipulator arms, controlled by the driver mechanism of this invention, use a pair of pliable, flat smooth pads or surfaces between which is positioned a spherical member, such as a hollow glass or metal microsphere used in inertial confinement fusion targets, for inspection of the outer surface and/or interior of the microsphere. The manipulator arm pads or surfaces for retaining the microsphere may be made, for example, as described and claimed in the above-referenced copending application Ser. No. 906,815. Also, while the invention is described hereinafter as being utilized for examination of microspheres, such as glass spheres used in the fabrication of inertial confinement fusion targets, it is not intended to limit the invention to any specific application since it can be utilized whereever there is a requirement for controllably rolling a spherical member in two perpendicular horizontal directions.

Figure 1A:
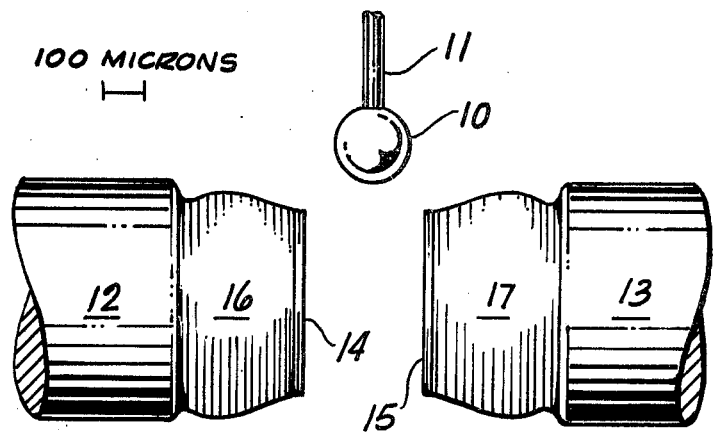
FIGS. 1a-1c illustrate an operational sequence of a pair of manipulator arms controlled by the driver mechanism of the present invention.
Figure 1B:
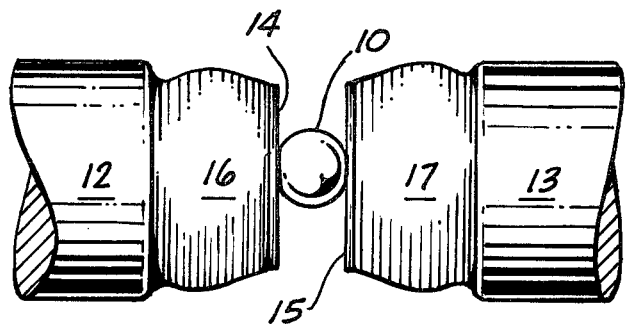
Figure 1C:
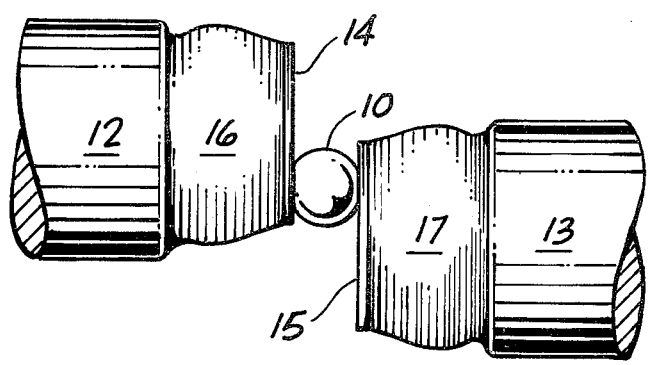

FIGS. 1a-1c illustrate, in enlarged view, an embodiment of a manipulator for microspheres controlled by the driver mechanism of the present invention. In FIG. 1a, a microsphere ($\mu$sphere) 10 retained by a vacuum chuck 11 is inserted between manipulator arms or carriers 12 and 13 having soft, flat end pads or tips 14 and 15, respectively, secured via capillary tubes 16 and 17. For example, the pads 14 and 15 may be constructed of silicone rubber and be about 0.5 mm in diameter. FIG. 1b shows the manipulator arms 12 and 13 moved together such that the pads 14 and 15 grasp the microsphere 10, whereupon vacuum chuck 11 is removed. FIG. 1c illustrates the translation of the manipulator arms 12 and 13, in equal amounts in opposite directions, such that microsphere 10 is rolled about its center by pads 14 and 15 without overall motion of the microsphere. Moving the arms in two perpendicular directions, by the driver mechanism described hereinafter, provides rotation of the microsphere about two orthogonal axes.

Figure 2:
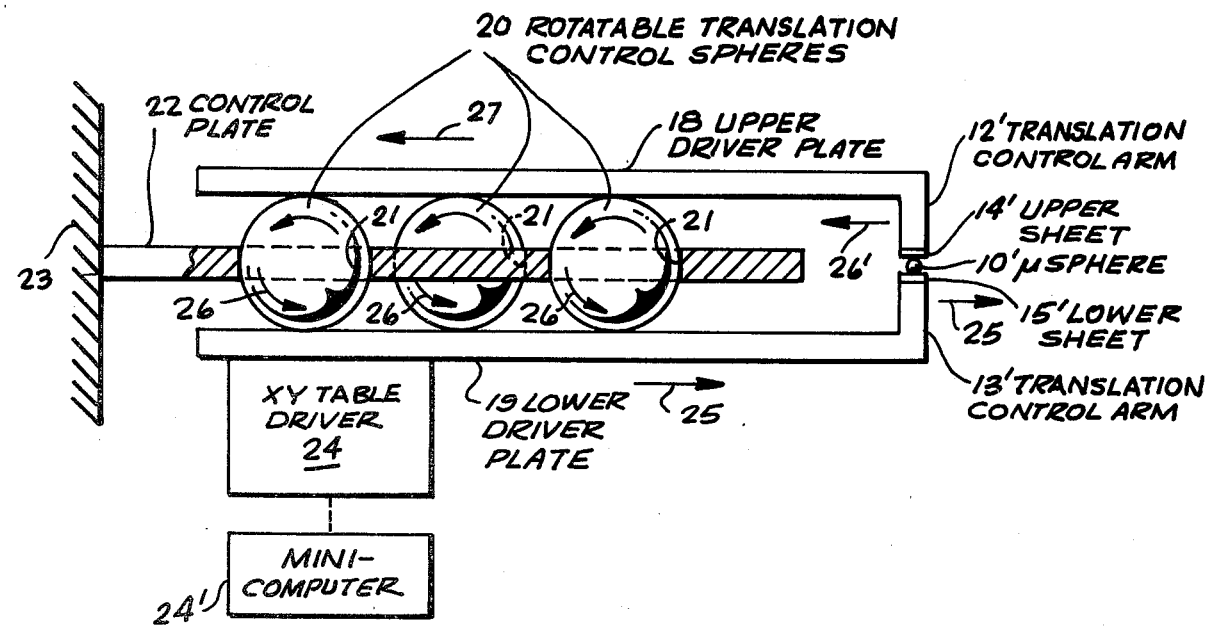
FIG. 2 schematically illustrates an embodiment of a driver mechanism made in accordance with the invention.
Figure 3:
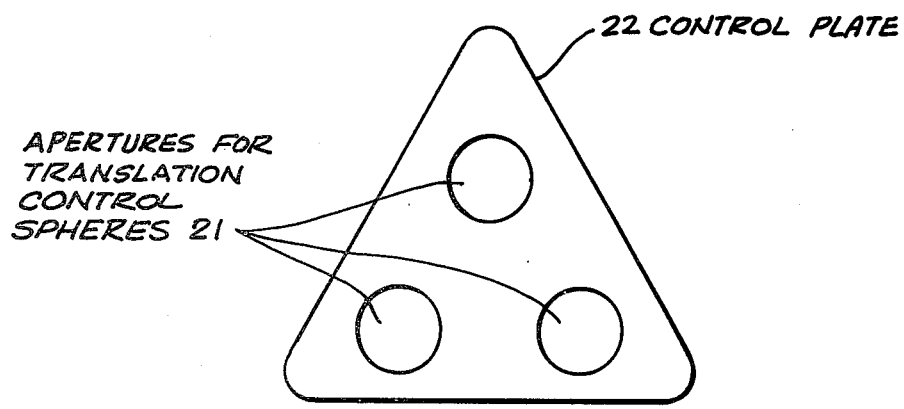
FIG. 3 is a plan view of the control plate of the FIG. 2 embodiment.

Referring now to FIGS. 2 and 3, the embodiment of the x- and y-axis driver mechanism comprises a pair of translation control or manipulator arms 12' and 13' having flat, smooth pads or sheets 14' and 15' secured thereto for retaining therebetween a microsphere 10' to be examined by mechanism, such as an interferometer, not shown; the arms 12' and 13' are rigidly attached to an upper driver plate 18 and a lower driver plate 19, respectively; the upper and lower driver plates 18 and 19 being held in parallel relationship by three rotatable translation spheres 20 in frictional contact therewith, with the spheres 20 (0.5 cm to 3 cm diameter) being held firmly but rotatably in three apertures 21 in a control plate 22 which is fixedly secured at one end to a support structure 23. The lower driver plate 19 is mounted on an x-y stage table driver 24, driven for example by stepping motors which may be controlled by a programmed minicomputer 24'. The controlling computer program can drive the manipulator arms in any desired scan pattern for the microsphere. The mechanism may also have a manual control which can be used instead of a programmed scan for inspecting some particular defect in detail.

In operation, as the lower drive plate 19 moves, say, to the right, as indicated by arrow 25, in response to a force applied by the x-y table driver 24, the three translation control spheres 20 rotate counterclockwise, as indicated by arrows 26; and this causes the upper drive plate 18 to move to the left, as indicated by arrow 27, by precisely the same distance as the lower drive plate 19 moves to the right. The translation control arms 12' and 13', of course, follow the motion of the respective driver plates, as indicated by arrows 25' and 26', and this ultimately causes the microspheres 10' to rotate controllably between the upper and lower sheets 14' and 15'.

Tests conducted on apparatus constructed as in the above-described FIGS. 2 and 3 embodiment allow very tight control on the positioning of the microsphere utilizing the pads or sheets illustrated in FIGS. 1a–1c for retaining the microsphere, with associated backlash in the driver mechanism being less than 0.5 microns. Motion in each of the two perpendicular (x-, y-) horizontal directions provided excellent rotation of the microsphere for examination purposes.

It has thus been shown that the present invention provides an x- and y-axis driver mechanism for precise rotation and control of a spherical member, thus enabling rapid and full inspection of the spherical member, for example.

While a particular embodiment of the invention has been described and illustrated, modifications will become apparent to those skilled in the art, and it is intended to cover in the appended claims, also such modifications as come within the spirit and scope of the invention.

What is claimed is:

1. A x- and y-axis driver mechanism for control of the motion and position of a spherical member comprising: a pair of arms, each of said arms being constructed at one end thereof to retain an associated spherical member therebetween, one of said pair of arms being fixedly connected at the opposite end to a first movable driver plate, the other of said pair of arms being fixedly connected at the opposite end to a second movable driver plate spaced from said first driver plate, a fixed control plate positioned intermediate said first and second driver plates and provided with a plurality of apertures therein, a plurality of spheres rotatably positioned in said apertures of said control plate and constructed such that the outer periphery thereof contacts said first and second driver plates, and an x-y table driver operatively connected to said second driver plate, whereby movement of said second driver plate in a horizontal direction by said x-y table driver causes rotation of said plurality of spheres and movement of said first driver plate in an opposite horizontal direction, such that said arms move in opposite directions so as to cause a rolling motion of an associated spherical member retained therebetween.

2. The driver mechanism defined in claim 1, additionally included a programmed minicomputer operatively connected to said x-y table driver so as to drive said arms in any desired horizontal pattern.

3. The driver mechanism defined in claim 1, wherein said control plate is triangular in configuration.

4. The driver mechanism defined in claim 3, wherein said plurality of spheres consist of three spheres positioned in triangularly spaced apertures in said control plate.

5. The driver mechanism defined in claim 1, wherein said arms are each provided at one end thereof with a flat, smooth pad for retaining and rolling an associated spherical member.

* * * * *